US011071602B2

(12) United States Patent
Pereira et al.

(10) Patent No.: US 11,071,602 B2
(45) Date of Patent: Jul. 27, 2021

(54) SCOPE DEVICES AND METHODS

(71) Applicant: Boston Scientific Scimed, Inc., Maple Grove, MN (US)

(72) Inventors: Peter J. Pereira, Mendon, MA (US); Adam P. Nodiff, Southborough, MA (US); Wen-Jui Ray Chia, Sunnyvale, CA (US); Michael O'Brien, Newton, MA (US); Kimberly DeGraaf, Holden, MA (US); Chad Schneider, Owings Mills, MD (US); Jozef Slanda, Milford, MA (US); Christopher P. Gauvin, South Grafton, MA (US); James M. Goddard, Pepperell, MA (US); Brandon W. Craft, Edgewater, MD (US); Timothy P. Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 393 days.

(21) Appl. No.: 16/027,872

(22) Filed: Jul. 5, 2018

(65) Prior Publication Data
US 2019/0008601 A1   Jan. 10, 2019

Related U.S. Application Data

(60) Provisional application No. 62/529,311, filed on Jul. 6, 2017.

(51) Int. Cl.
*A61B 1/018*  (2006.01)
*A61B 1/045*  (2006.01)
(Continued)

(52) U.S. Cl.
CPC ............ *A61B 34/74* (2016.02); *A61B 1/0052* (2013.01); *A61B 1/015* (2013.01); *A61B 1/018* (2013.01);
(Continued)

(58) Field of Classification Search
CPC ....... A61B 34/74; A61B 1/0052; A61B 1/015; A61B 1/018; A61B 1/045; A61B 18/24;
(Continued)

(56) References Cited

U.S. PATENT DOCUMENTS

| 5,514,131 A | 5/1996 | Edwards et al. |
| 5,718,702 A | 2/1998 | Edwards |

(Continued)

FOREIGN PATENT DOCUMENTS

| EP | 2 572 669 | 3/2013 |
| JP | 2007151595 | 6/2007 |

(Continued)

OTHER PUBLICATIONS

International Search Report on Patentability and Written Opinion issued in International Application No. PCT/US2018/040903, dated Jan. 17, 2019 (12 pages).

*Primary Examiner* — Timothy J Neal
*Assistant Examiner* — William B Chou
(74) *Attorney, Agent, or Firm* — Bookoff McAndrews, PLLC

(57) ABSTRACT

A device or scope device is disclosed. The device may comprise: a handle body extending along an axis between first end and a second end; an actuator at the first end of the handle body; a catheter at the second end of the handle body; and a processing unit communicable with a plurality of devices to: switch-in the actuator for control of one device of the plurality of devices; configure, with the actuator, a setting of the one device, control, with the actuator, the one (Continued)

device based on the setting, and switch-in the actuator for control of another one of the plurality of devices. Related devices and methods also are disclosed.

20 Claims, 5 Drawing Sheets

(51) Int. Cl.
    *A61B 34/00*     (2016.01)
    *A61B 1/005*     (2006.01)
    *A61B 1/015*     (2006.01)
    *A61B 18/24*     (2006.01)
    *A61M 25/01*     (2006.01)
    *A61B 18/00*     (2006.01)

(52) U.S. Cl.
    CPC .............. *A61B 1/045* (2013.01); *A61B 18/24* (2013.01); *A61M 25/0136* (2013.01); *A61B 2018/00011* (2013.01); *A61B 2018/00916* (2013.01); *A61B 2018/00928* (2013.01); *A61B 2018/00952* (2013.01); *A61B 2018/00958* (2013.01); *A61B 2018/00982* (2013.01); *A61B 2034/742* (2016.02); *A61B 2218/002* (2013.01)

(58) Field of Classification Search
    CPC .... A61B 2034/742; A61B 2034/00011; A61B 2034/00916; A61B 2034/00928; A61B 2034/00952; A61B 2034/00958; A61B 2034/00982; A61B 2218/002; A61M 25/0136

See application file for complete search history.

(56) References Cited

U.S. PATENT DOCUMENTS

| | | | |
|---|---|---|---|
| 6,434,416 B1 * | 8/2002 | Mizoguchi | G02B 21/0012 600/427 |
| 6,682,426 B2 | 1/2004 | Goto et al. | |
| 8,202,268 B1 | 6/2012 | Wells et al. | |
| 2007/0219806 A1 * | 9/2007 | Yamaki | A61B 17/00 704/275 |
| 2008/0154249 A1 | 6/2008 | Cao | |
| 2009/0149709 A1 | 6/2009 | Koitabashi | |
| 2009/0209810 A1 * | 8/2009 | Endo | A61B 1/045 600/109 |
| 2013/0067725 A1 | 3/2013 | Behnke et al. | |
| 2015/0073452 A1 * | 3/2015 | Uchida | A61B 17/3203 606/167 |
| 2016/0166129 A1 | 6/2016 | Walish et al. | |
| 2016/0213387 A1 | 7/2016 | DeGraaf et al. | |
| 2016/0262597 A1 | 9/2016 | Danchinyu et al. | |
| 2019/0000567 A1 * | 1/2019 | Allen | A61B 34/30 |

FOREIGN PATENT DOCUMENTS

| | | |
|---|---|---|
| WO | WO 97/41786 | 11/1997 |
| WO | WO 2017/003514 A1 | 1/2017 |

* cited by examiner

SCOPE DEVICES AND METHODS

CROSS-REFERENCE TO RELATED APPLICATIONS

This application claims the benefit of priority to U.S. Provisional Application No. 62/529,311, filed Jul. 6, 2017, which is incorporated by reference herein in its entirety.

TECHNICAL FIELD

Aspects of the present disclosure generally relate to scope devices and methods. Particular aspects relate to controlling other devices with a scope device.

BACKGROUND

Numerous devices may be used by a surgeon in a surgical procedure to perform treatments and sustain a patient. For example, one device may be a fluid pump configured to deliver a fluid to a body cavity within the patient, and another device may be a laser generator configured to direct laser energy into the body cavity. The fluid may expand the body cavity (e.g., like a balloon); and the laser energy may ablate a target in the cavity (e.g., a stone). Each source typically has controls located remotely from the patient. For example, both the fluid pump and the laser generator typically have device-specific controllers located outside of a sterile field.

As a result, Additional operators may be required to use the device-specific controllers, potentially reducing the efficiency of the surgical procedure and increasing costs. Some inefficiencies may be attributable to the challenges of communications between the surgeon and the additional operators. Other inefficiencies may be attributable to the challenges of learning how to use multiple device-specific controllers prior to the medical procedure, and/or switching between the multiple device-specific controls during the procedure. Both challenges create opportunities for error.

The scope devices and methods described herein address these challenges and remedy other deficiencies in the prior art.

SUMMARY

One aspect of the present disclosure is a device. The device may comprise: a handle body extending along an axis between first end and a second end; an actuator at the first end of the handle body; a catheter at the second end of the handle body; and a processing unit communicable with a plurality of devices to: switch-in the actuator for control of one device of the plurality of devices; configure, with the actuator, a setting of the one device, control, with the actuator, the one device based on the setting, and switch-in the actuator for control of another one of the plurality of devices.

In some aspects, the device may further comprise: a port on the second end of the handle body; and a lumen extending from the port, through the second end of the handle body, and through the catheter. The catheter may include a steerable portion, and the device may further comprise a steering actuator operable to control the steerable portion of the catheter. The actuator may comprise a selection toggle operable with the processing unit to switch-in the one device; and the selection toggle may include one of a button, a joystick, a switch, and a trigger.

According to this disclosure, the actuator may comprise a program toggle operable with the processing unit to execute a control program for the one device. For example, the processing unit may be communicable with the plurality of devices to switch-in the actuator for control of the one device together with at least one other device of the plurality devices. The actuator may comprise a trigger that is (i) pivotally mounted to the handle body, and (ii) operable to control the one device based on a rotational position of the trigger relative to the handle body.

The one device may include a imaging device; and the processing unit may be communicable with the imaging device to control, with the actuator, activation of the imaging device. The one device also may include a fluid source configured to deliver a fluid flow through the catheter; and the processing unit may be communicable with the fluid source to control, with the actuator, at least one property of the fluid flow. For example, the at least one property of the fluid flow may include a flow rate or a pressure of the fluid flow. The one device also may include a laser source configured to deliver laser energy through the catheter; and the processing unit may be communicable with the laser source to control, with the actuator, at least one property of the laser energy. The at least one property of the laser energy may include a frequency or a power level of the laser energy. The one device also may include a peripheral device, and the processing unit may be communicable with the peripheral device to control, with the actuator, an electrical or mechanical component of the peripheral device. The peripheral device may be removably engageable with the second end of the handle body.

Another aspect of this disclosure is a device. The device may comprise: a handle body extending along an axis between first end and a second end; a control actuator and a steering actuator at the first end of the handle body; a catheter at the second end of the handle body, the catheter including a steerable portion operable with the steering actuator; a port at the second end of the handle body; a lumen extending from the port, through the second end of the handle body, and through the catheter; and a processing unit communicable with a plurality of devices to: switch-in the actuator for control of one device of the plurality of devices; configure, with the actuator, a setting of the one device, control, with the actuator, the one device based on the setting, and switch-in the actuator for control of another one of the plurality of devices.

In other aspects, the actuator may comprise a trigger that is pivotally mounted to the handle body, and operable to control the one device based on a rotational position of the trigger relative to the handle body. In some aspects, the actuator may comprise a selection toggle operable with the processing unit to switch-in the one device, and a program toggle operable with the processing unit to execute a control program for the one device. The one device may include an imaging device; and the processing unit may be communicable with the imaging device to control, with the actuator, activation of the imaging device. The processing unit may remain in communication with at least one other device of the plurality of devices when the actuator is switched-in for control of the one device. The one device may include (i) a fluid source configured to deliver a fluid flow through the lumen, and (ii) a laser source configured to deliver laser energy through the lumen; and the processing unit may be communicable with the fluid source and the laser source to control, with the actuator, the fluid flow and the laser energy. For example, the actuator may comprise a program toggle operable with the processing unit to execute a control program for controlling the fluid source together with the laser source.

Yet another aspect of this disclosure is a device comprising: a handle body extending along an axis between first end and a second end; an actuator at the first end of the handle body; a catheter at the second end of the handle body; a peripheral device at the second end of the handle body, the peripheral device including a wire and a motor configured to move the wire relative to the catheter; and a processing unit communicable with a plurality of devices to: switch-in the actuator for control of one device of the plurality of devices; configure, with the actuator, a setting of the one device, control, with the actuator, the one device based on the setting, and switch-in the actuator for control of another one of the plurality of devices, wherein the one device includes the motor of the peripheral device. In some aspects, for example, a distal end of the wire may include a basket, and the motor may be configured to move the basket relative to the catheter.

BRIEF DESCRIPTION OF THE DRAWINGS

The accompanying drawings are incorporated in and constitute a part of this specification. These drawings illustrate exemplary aspects of this disclosure that, together with the written descriptions herein, serve to explain this disclosure as follows.

DETAILED DESCRIPTION

Aspects of the present disclosure are now described with reference to numerous scope devices and methods. Some aspects are described with reference to surgical procedures where an energy and/or fluid are delivered to a body cavity. For example, some aspects may be described with reference to an laser energy and/or a fluid flow that are delivered to a kidney, and configured to treat a kidney stone located in the kidney. References to a particular type of procedure, energy, fluid, cavity, or stone are provided for convenience and not intended to limit the present disclosure unless claimed. Accordingly, the concepts described herein may be used for any analogous devices or methods, surgical or otherwise.

Numerous axes and directions are described. Each axis may be transverse, or even perpendicular, with the next so as to establish a Cartesian coordinate system with an origin point 0. One axis may extend along a longitudinal axis of an element. Relative locations and directions may be indicated by the terms "proximal" and "distal," and their respective initials "P" and "D." Proximal refers to a position closer to the exterior of the body or a user, whereas distal refers to a position closer to the interior of the body or further away from the user. Appending the initials P or D to an element number signifies a proximal or distal location, and appending P or D to an arrow in a figure signifies a proximal or distal direction along an axis. The term "elongated" may refer to any object that is substantially longer in relation to its width, such as an object having a length that is at least two times longer than its width along its longitudinal axis. Some elongated objects, for example, are axially extending in a proximal or distal direction along an axis. Unless claimed, these terms are provided for convenience and not intended to limit this disclosure to a particular location, direction, or orientation.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements. Terms such as "generally," "about," "substantially," and/or "approximately" indicate a range of possible values that are within +/−5% of a stated value.

Figure 1A:
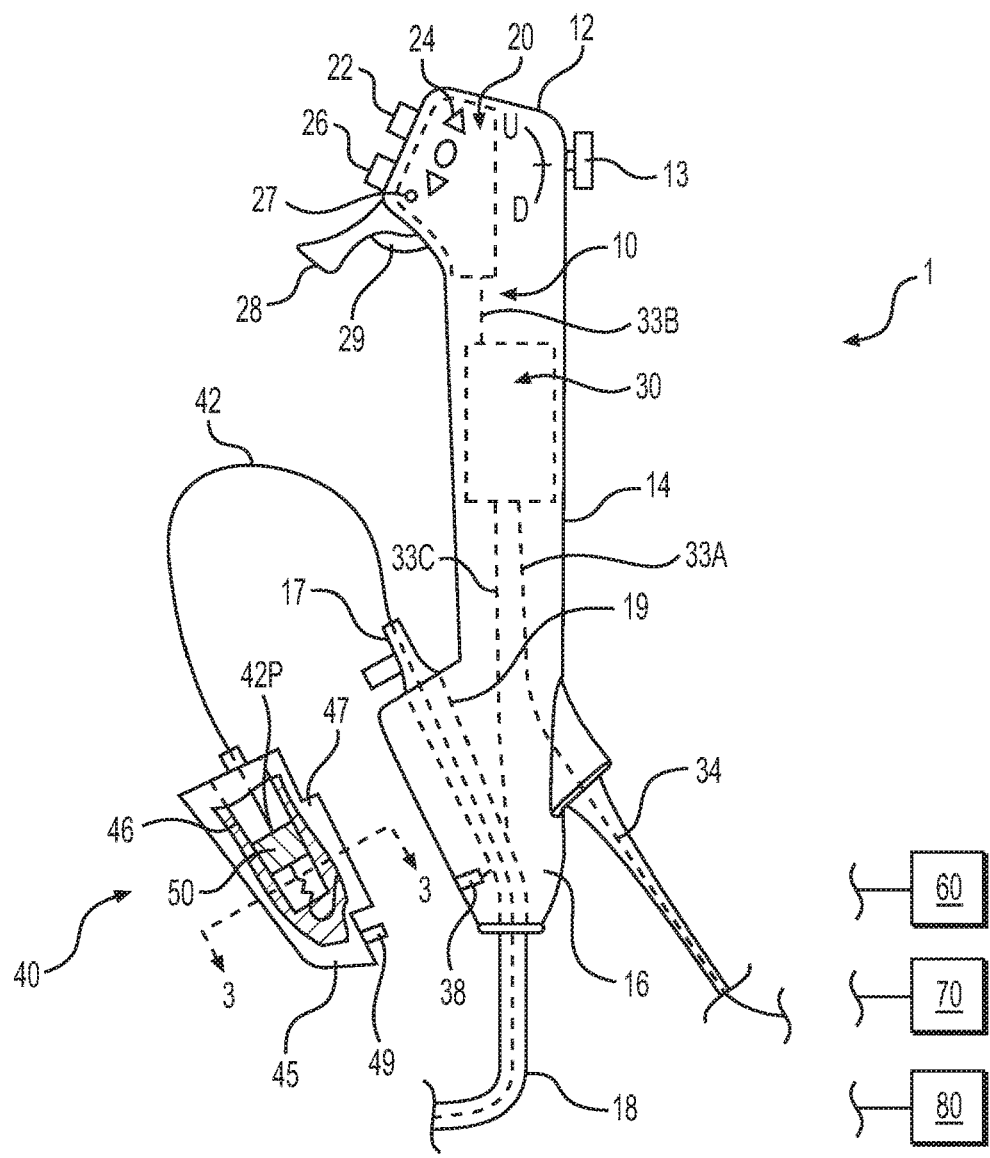
FIG. 1A depicts a scope device and a peripheral device attached thereto according to aspects of the present disclosure.
Figure 2:
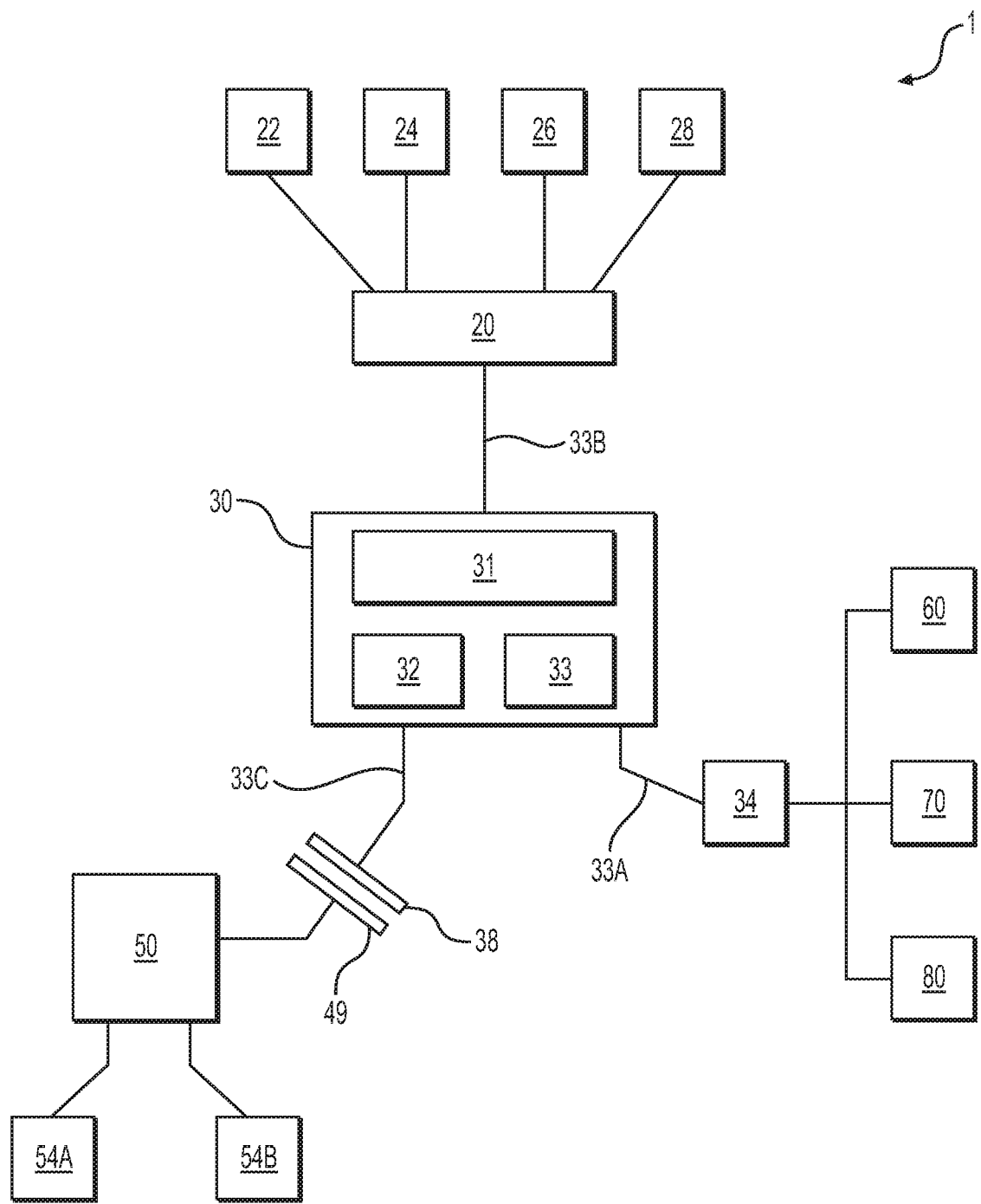
FIG. 2 depicts a processor associated with the scope device of FIG. 1A.

One aspect of the present disclosure is now described with reference to a scope device 1. As shown in FIG. 1A, scope device 1 may comprise a handle body 10; an actuator 20; and a processing unit 30. Aspects of handle body 10 may be specialized for use in certain medical procedures. For example, handle body 10 of FIG. 1A includes a port 17, a catheter or flexible tube 18, and a lumen 19 extending through said catheter or tube, making handle body 10 suitable for use in non-invasive procedures. As shown in FIGS. 1A and 2, processing unit 30 may be in communication with a plurality of devices including, for example, a peripheral device 40, a display device 60, a fluid source 70, a laser source 80, or any other electronic device common to medical procedures, including imaging devices, sensory devices, and the like. According to this disclosure, processing unit 30 may be configured to switch-in actuator 20 for control of one or more devices of the plurality of devices, allowing scope device 1 to serve as a universal controller.

Figure 4:
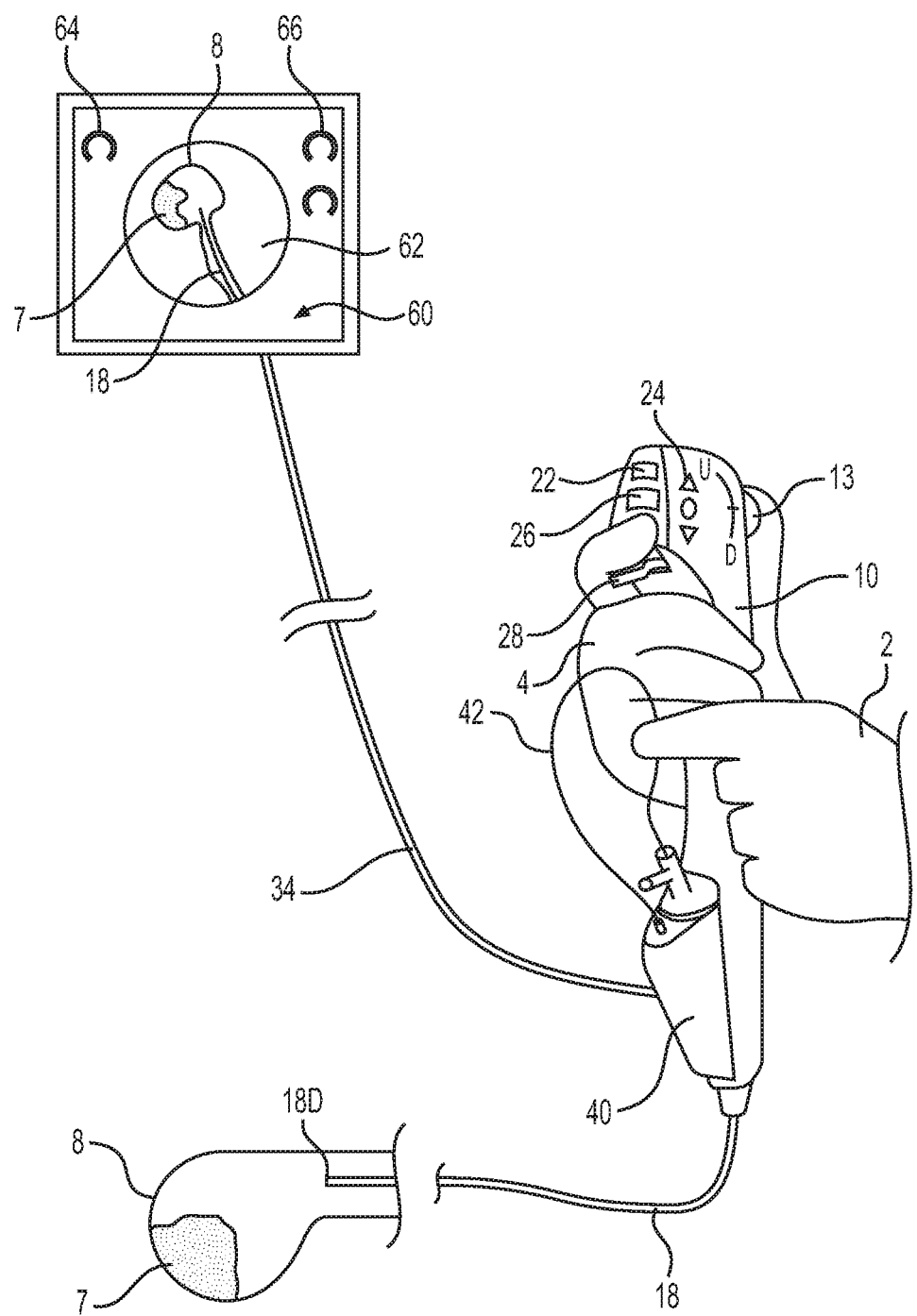
FIG. 4 depicts methods of operating of the device of FIG. 1 according to aspects of the present disclosure.

Handle body 10 is depicted in FIG. 1A as including a central portion 14 extending longitudinally between a first end 12 of body 10, and a second end 16 of body 10. As shown in FIG. 4, central portion 14 may be grasped by a hand 4 in a upright or trigger-grip manner, such that first end 12 is located above or superior to second end 16, and second end 16 is located below or inferior to first end 12. In this configuration, aspects of actuator 20 may be operable with digits of hand 4 when central portion 14 is grasped within the palm of hand 4, leaving hand 2 free. Handle body 10 may include one or more interior cavities, and/or one or more channels extending between each interior cavity, as described further below.

Actuator 20 may be located at first end 12 of handle body 10, and configured to output control signals to processing unit 30 when operated by hand 4. As shown in FIG. 1A, actuator 20 may include physically movable portions, which may extend through an opening in handle body 10. For example, actuator 20 may include any combination of buttons, knobs, levers, switches, triggers, and the like. Actuator 20 also may include tactile sensors (e.g., touchscreens) configured to output similar control signals without considerable physical movement.

An exemplary actuator 20 is depicted in FIG. 1A as comprising: a selection toggle 22; a configuration interface 24; a program toggle 26; and a trigger 28. Selection toggle 22 may include a button extending through a front surface of first end 12, or a tactile sensor (e.g., a touchscreen) mounted on said front surface. Configuration interface 24 may include a plurality of buttons extending through an exterior or side surface of first end 12, or an tactile sensor mounted on said surfaces. As shown in FIG. 1A, interface 24 may include an up movement button, a central selection button, and a downward movement button, each of which may be used to navigate lists on, for example, a display 60 of FIG. 4. Program toggle 26 may be identical to selection toggle 22. For example, toggles 22 and 26 may be independently movable buttons, or separate portions of a touchscreen.

Figure 1B:
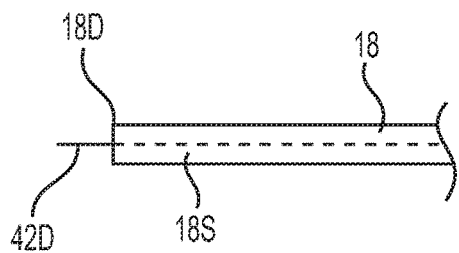
FIG. 1B depicts a distal end of a catheter of the scope device of FIG. 1A.
Figure 1C:
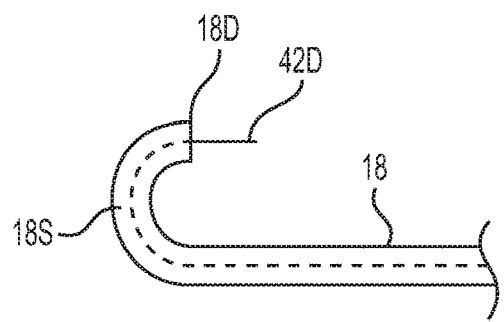
FIG. 1C depicts the distal end of FIG. 1B in a different configuration.

Trigger 28 may be pivotally mounted to handle body 10. As shown in FIG. 1, for example, a first end of trigger 28 may be attached to a pivot axle 27 located within handle body 10. This configuration allows a second end of trigger 28 to be rotated relative to actuator 20 between a first or open position, wherein the second end of trigger 28 is away from the handle body 10; and a second or closed position, wherein the second end of trigger 28 is toward body 10. As shown in FIG. 4, a digit of hand 4 may be used to move trigger 28 toward or away from handle body 10 to realize the open and closed positions. A biasing actuator 29 may be located behind trigger 28. Actuator 29 may include a resilient element (e.g., a spring) configured to bias trigger 28 towards to the open position, and/or a motion sensor (e.g., a tilt sensor) configured to output a signal to processing unit 30 based on the position of trigger 28 relative to actuator assembly 30. The resilient element may apply a continuous and/or variable biasing force to trigger 28, allowing for smooth and/or variable operation. Biasing element 29 also may include an incrementing mechanism (e.g., gears or ratchets) allowing for controlled movements of trigger 28 relative to handle body 10.

The second end 16 of handle body 20 may include a port 17 that permits delivery of items and/or substances into a patient. Port 17 may be in communication with additional delivery means. As shown in FIG. 1A, catheter or flexible tube 18 may extend away from second end 16, and a lumen 19 may extend from port 17, through second end 16, and into catheter 18, placing port 17 in communication with catheter 18. As further shown in FIGS. 1B and 1C, catheter 18 may include a distal end 18D, and a steerable portion 18S located proximal of distal end 18D. Steerable portion 18S may be movable between a first or straight position, as in FIG. 1B; and a second or bent position, as in FIG. 1C. Device 10 may further comprise a steering actuator 13 operable to control steerable portion 18S. In FIG. 1A, steering actuator 13 is attached to first end 12 of handle body 10, and operable to move steerable portion 18S between various first and second positions. For example, steering actuator 13 may operate steerable portion 18S through a mechanical linkage (e.g., gears, wires, etc.) and/or an electrical linkage (e.g., motor(s)) contained inside of handle body 10, either of which may be coupled to one or more steering wires extending through catheter 18.

Processing unit 30 may be mounted in handle body 10. An exemplary processing unit 30 is depicted in FIG. 2A as comprising: one or more processors 31; a memory 32; and a transceiver 33. The one or more processors 31 may be local to or remote from processing unit 30. For example, one portion of processors 31 may be local to actuator 20, while another portion of processors 31 is local to processing unit 30, each portion being in constant communication with each other and/or a plurality of other devices over a network. Memory 32 may be configured to store program instructions executable by the one or more processors 31. Portions of memory 32 also may be local to or remote from processing unit 30.

Transceiver 33 may comprise any wired or wireless means for sending and receiving data. As shown in FIGS. 1A and 2A, for example, transceiver 33 may comprise a first set of wires 33A connecting one or more processors 31 to a data and power source 34, a second set of wires 33B connecting unit 31 to actuator 20, and third set of wires 33C connecting unit 31 to a peripheral device interface 38. Each set of wires 33A, 33B, and 33C may be a combined data and power cable (e.g., a USB cable) that is routed through an interior cavity or channel within handle body 10. External data and power source 34 may be another combined data and power cable (e.g., a USB cable) engageable with external sources of data and power.

Although not required, scope device 1 of FIG. 1A further comprises a peripheral device 40 that is removably mounted to or engageable with handle body 10. Peripheral device 40 may be any device that electrical components (e.g., motors, sensors, etc.) operable with actuator 20. As shown in FIG. 1A, device 40 may comprise: a wire element 42; a housing 45; and at least one motor 50. Exemplary aspects of each element of peripheral device 40 are now described.

Figure 5A:
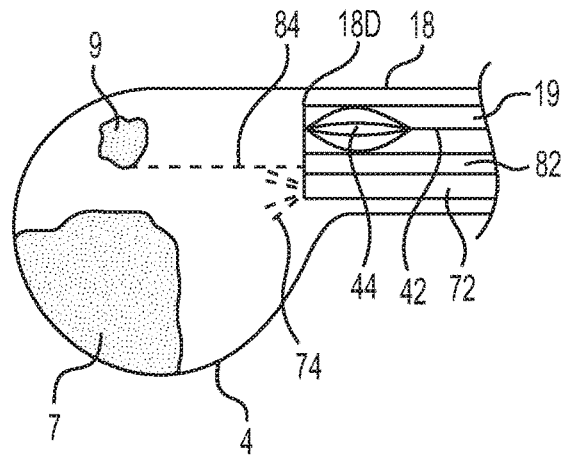
FIG. 5A depicts methods of determining a target.
Figure 5B:
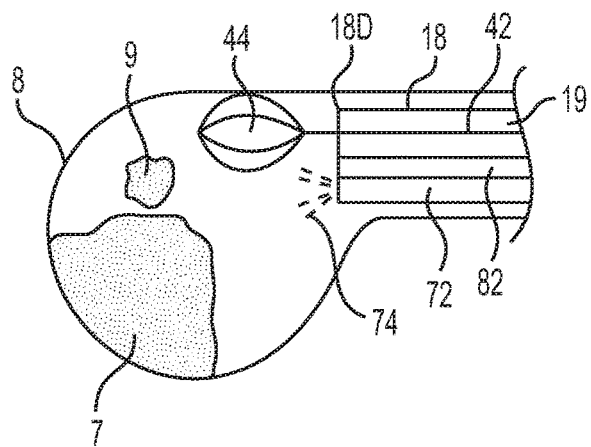
FIG. 5B depicts methods of capturing the target.
Figure 5C:
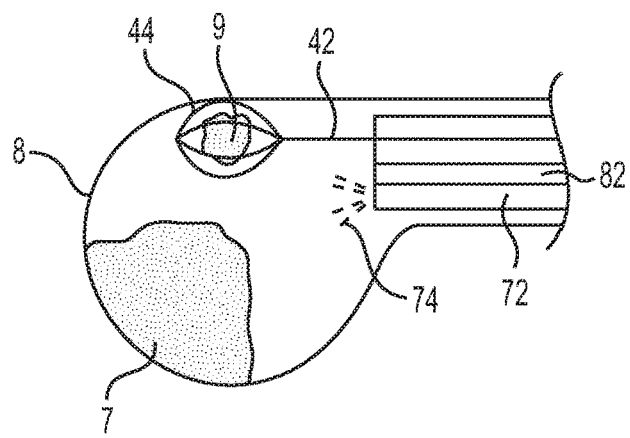
FIG. 5C depicts methods of removing the target.

Wire element 42 may comprise any elongated object, such as an electrical coil or conductor, an optical fiber, a rod, a wire, or the like. As shown in FIG. 1A, wire element 42 may include a proximal end 42P in housing 45; and a flexible body extending distally from proximal end 42P, into port 17, and through lumen 19 until and a distal end 42D of wire element 42 is located at the distal end 18D of catheter 18. Proximal end 42P of wire element 42 may be coupled to the at least one motor 50 inside housing 45. As shown in FIGS. 5A-C, distal end 42D may have an end effector 44 attached thereto. End-effector 44 may include a self-expanding basket and/or any retrieval or capture device, such as a grasper, a hook, scissors, or the like.

Figure 3:
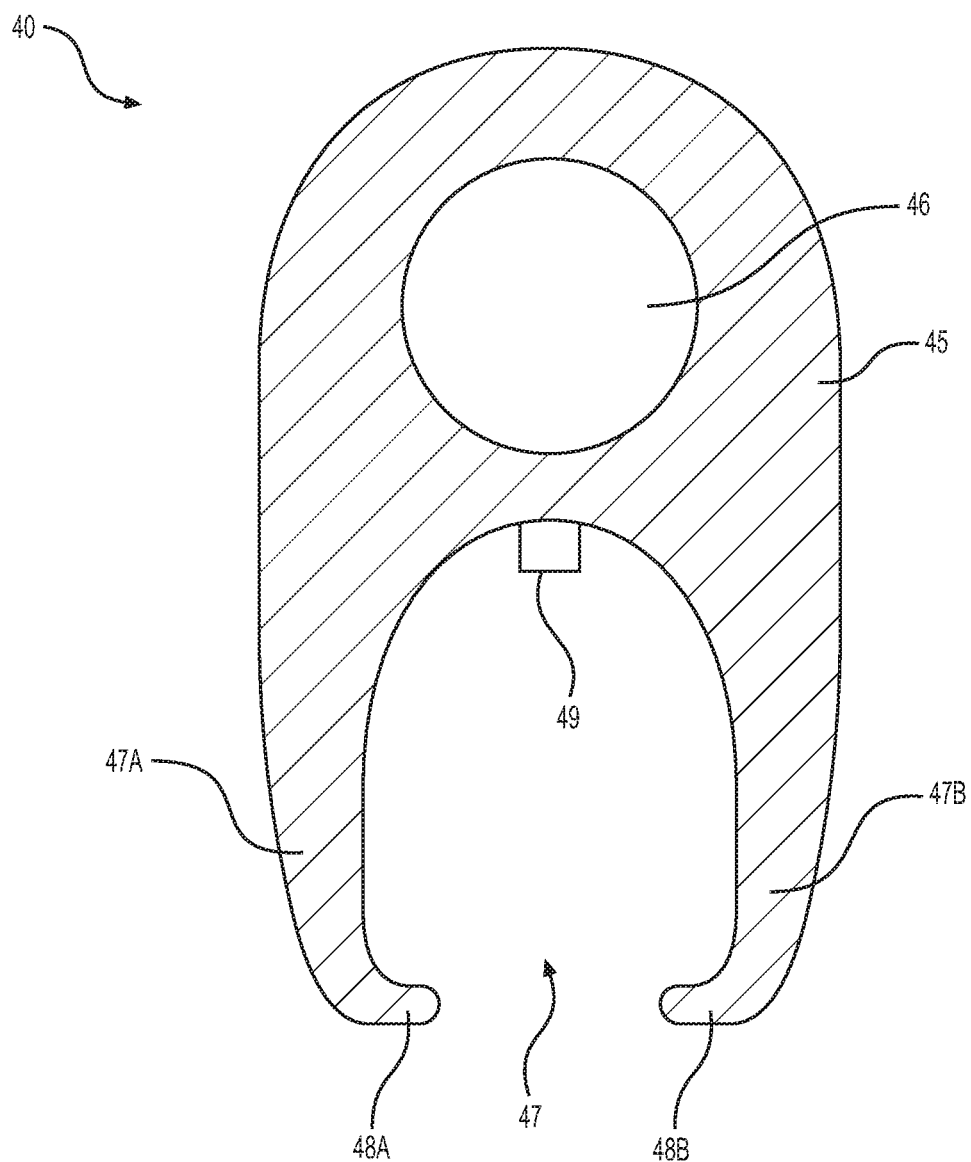
FIG. 3 depicts a cross-section of the peripheral device of FIG. 1A taken along Section Line 3-3 of FIG. 1A.

Housing 45 may be removably attached to handle body 10. As shown in FIGS. 1A and 3, housing 45 may comprise: an interior cavity 46; a mounting structure 47; and a scope device interface 49. Interior cavity 46 may be cylindrical cavity extending through housing 45. Mounting structure 47 may comprise a pair of opposing arms 47A and 47B that are removable engageable with second end 16 of handle body 10. For example, each arm 47A and 47B of FIG. 3 includes a protrusion 48A or 48B engageable with a recess formed on an exterior surface of second end 16, allowing housing 45 to be snapped onto handle body 10. Scope device interface 49 may be engaged with peripheral device interface 38 when mounting structure 47 is engaged with second end 16. For example, peripheral device interface 38 may be a female USB connection, and scope device interface 49 may be male USB connection that plugs into the female USB connection when housing 45 is snapped onto handle body 10. Housing 45, like handle body 10, may include openings and/or channels configured to accommodate wires extending between motor 50 and scope device interface 49.

At least one motor 50 may be located within interior cavity 46 of housing 45 and operable to move wire element 42. For example, as shown in FIG. 1A, at least one motor 50 may be coupled to the proximal end 42P of wire element 42 and operable with actuator 20 to move wire element 42 in a translational direction and/or a rotational direction relative to housing 45. A combined data and power cable 52 may extend between motor 50 and scope device interface 48, allowing power and/or control signals to be sent from processor 30 to motor 50 when scope device interface 48 is engaged with peripheral device interface 38.

Processing unit 30 may be communicable with a plurality of devices. A number of exemplary devices are depicted in FIG. 1A, including peripheral device 40, display 60; fluid source 70; and laser source 80. In some aspects, processing unit 30 is communicable with the plurality of devices to: switch-in actuator 20 for control of one device of the plurality of devices (e.g., the fluid source); configure, with actuator 20, a setting of the one device; control, with actuator 20, the one device based on the setting, and/or switch-in actuator 20 for control of another one of the plurality of devices (e.g., the laser source). Processor unit 30 may be operable with display device 60 to switch-in the plurality of devices. For example, display 60 may include a list of the plurality of devices, configuration interface 24 may be used to select a device from list, and processing unit 30 may be configured to switch-in the selected device for control by actuator 20. Processing unit 30 may be further configured to receive a control mapping for each device, and apply the control mapping to actuator 20. Actuator 20 may be switched-in for control of one or more devices in this manner. Selection toggle 22 may be used to switch between the devices. For example, processing unit 30 may be configured to receive a first control mapping from a first device, and a second control mapping for a second device. The first and second control mappings may be stored in memory 32, and selection toggle 22 may be used to switch-in the first or second devices by switching between their respective first and second mappings.

Processing unit 30 may use the control mappings to associate portions of actuator 20 with a particular function of the paired device. Fluid source 70 may be configured to deliver a fluid flow through port 17, and actuator 20 may be operable to control at least one property of the fluid flow. For example, fluid source 70 may be a pump including a first control for a first property of the fluid flow (e.g., temperature or medicine content), a second control for a second property of the fluid flow (e.g., flow rate), and a control mapping that associates the first control with configuration interface 24 and the second control with trigger 28. Once mapped, configuration interface 24 may be operable with display device 60 to either select the first property from a list of potential settings (e.g., by using the up and down arrows to navigate a list, and the center selection button to make a selection); or to manually adjust the first property (e.g., by using the up and down arrows to manually increase the first property). Trigger 28 may, for example, be used to active the fluid flow.

Laser source 80 may be configured to deliver laser energy through port 17, and actuator 20 may likewise be operable to control at least one property of the laser energy. For example, laser source 80 may include a first control of a first property of the laser energy (e.g., frequency), a second control for a second property of the laser energy (e.g., power level), and a control mapping that associates the first control with configuration interface 24 and the second control with trigger 28. As before, configuration interface 24 may then be used to determine the first and/or second properties, and trigger 28 may be used to activate the laser energy.

Processing unit 30 may use the control mappings to identify or obtain programs for operating the paired device(s); identify an activation command for each program; and/or associate the activation command with program toggle 26. For example, the control mapping for fluid source 70 may include a clearing program configured to increase a flow or pressure of the fluid flow for an amount of time to clear the visual field of blood or particulate, the amount of time may be predetermined by the program and/or determined by a sensor (e.g., a visual sensor mounted on the distal end 18D of catheter 18), and program toggle 26 may be used to initiate the clearing program. Other programs may be similarly configured modify a temperature of the fluid flow relative to a sensor input (e.g., temperature sensor mounted on catheter 18), and program toggle 26 may be used to selectively activate each program. Similar results may be achieved with laser source 80. For example, the control mapping for laser source 80 may including a program configured to modify a frequency, a power lever, and/or pulse rate of the laser energy responsive to the fluid flow; and program toggle 26 may be used to selectively activate the program.

In some aspects, processing unit 30 may be further configured to receive the control mappings for sources 70 and 80, and identify (e.g., from the mappings) or obtain (e.g., from a server) one or programs for operating sources 70 and 80 in a pre-determined sequence whenever program toggle 26 is activated. Display 60 and/or a processor in communicate therewith may be configured to identify such programs, and make them available for selection via configuration interface 24 and execution via program toggle 26. Exemplary programs may automatically adjust a property of the fluid flow (e.g., temperature) relative to a property of the laser energy (e.g. intensity).

The plurality of devices also may include peripheral device 40, meaning that actuator 20 may be switched-in to control the at least one motor 50 of peripheral device 40 and/or any other electrical component of device 40. For example, the at least one motor of motor 50 may include a first control for one property of the movement (e.g., speed), a second control for another property of the movement (e.g., forward or backward), and a control mapping that associates the first control with configuration interface 24 and the second control with trigger 28. In this example, components of motor 50 may be switched-in separately or together by selection toggle 22, allowing actuator 20 to control the translation and/or rotation of wire element 42.

Processor 30 may use the control mapping for peripheral device 40 to identify or obtain programs specific to the capabilities of device 40, and program toggle 26 may be used to active these programs. For example, as shown in FIGS. 5A-C, program toggle 26 may be used to automatically deploy end-effector 44 by moving wire element 42 a pre-determined distance relative to lumen 18 in a distal direction, and/or automatically retract end-effector 44 by moving wire element 42 a predetermined distance in a proximal direction. In some aspects, scope device 1 include sensors configured to determine a curvature of lumen 18, and processing unit 30 may use the aforementioned program to adjust the pre-determined distance based on the curvature.

Aspects of display 60 also may be controlled by processing unit 30. As described above, for example, display 60 may be used to depict any type of list, and actuator 20 (e.g., configuration interface 24) may be used to navigate such lists. Processing unit 30 may generate some lists. For example, program toggle 26 may be used as a hotkey configured to instantly depict a pre-determined list of settings for a paired device, allowing for immediate changes mid-procedure. With laser source 80, for example, program toggle 26 may be used to bring up pre-populated list of common energy parameters (e.g., laser settings), allowing the surgeon to easily adjust those settings with configuration interface 24 mid-procedure.

As shown in FIG. 4, for example, display 60 may include a visualization portion 62 depicting a kidney 8 and/or a stone 7, a first control gauge 64, and a second control gauge 66. Gauges 64 and 66 may be associated controls or measurements for different devices (e.g., fluid source 70 and laser source 80), and/or different controls or measurements for the same device (e.g., motors 54A and 54B). Selection toggle 24 may automatically associate gauges 64 and/or 66 with whenever a device is switched-in for control by actuator 20. For example, gauge 64 may be associated with fluid source 70 whenever that device is switched-in; and gauge 66 may be associated with laser source 80 whenever that device is switched-in. The plurality of devices may include a visualization device (e.g., a camera mounted on distal end 18D of catheter 18), the visualization device may be used to generate visualization portion 62 of display 60, and actuator 20 may be configured to control the visualization device. For example, program toggle 26 may be used to tag selected areas of visualization portion 62 (e.g., a cleared calyx of kidney 8), execute programs for determining characteristics of stone 7 (e.g., size or type), and/or highlight said characteristics on portion 62.

To illustrate capabilities of scope device 1, exemplary methods of using scope device 1 together with peripheral device 40, fluid source 70, and laser source 80 are now described. These methods are described with reference to steps for removing a fragment 9 of a stone 7 from a kidney 8, although similar steps may be performed in other surgical procedures, using any combination of devices, for any target. As shown in FIGS. 5A-C, wire element 42 may extend through a first portion of lumen 19; a fluid delivery channel 72 may extend through a second portion of lumen 19; and an energy delivery channel 82 may extend through a third portion of lumen 19.

As shown in FIGS. 4 and 5A-C, one exemplary method may comprise: pairing scope device 1 with peripheral device 40, fluid source 70, and/or laser source 80 (a "pairing step"); locating the distal end 18D of catheter 18 in kidney 8 opposite of stone 7 (a "locating step"); using selection toggle 22 to switch-in laser source 80 (a "first switching step"); using configuration interface 24 to configure laser source 80 (a "first configuration step"); and using trigger 28 to deliver an laser energy 84 to stone 7 through energy delivery channel 82 until a fragment 9 breaks away from stone 7 (a "treatment step"). The pairing step may be performed once for many devices, or once for each device. The locating step may comprise using lever 13 to move steerable portion 18S of catheter 18. In some aspects, the locating step also may comprise using toggle 22 to switch-in peripheral device 40; trigger 28, for example, to move wire element 42 therewith; and/or using program toggle 26 to active various movement programs. The treatment step may comprise: using selection toggle 22 to switch-in fluid source 70 for delivery of a fluid flow 74 into body cavity 4 through fluid delivery channel 72; and/or using program toggle 26 to activate various programs for delivering fluid flow 74 and laser energy 84 together or in sequence.

As shown in FIGS. 5B and 5C, another exemplary method may comprise: using selection toggle 22 to switch-in peripheral device 40 (a "second switching step"); using configuration interface 24 to configure motor 50 (a "second configuration step"); using trigger 28 to move wire element 42 until end-effector 44 has been extended from lumen 28 (a "moving step," as in FIG. 5B); and capturing stone fragment 6 with end-effector 44 (a "capture step," as in FIG. 5C). The moving step may comprise using program toggle 26 to execute programs for automatically extending end-effector 45 out of catheter 18. In some aspects, the moving step may further comprise; using selection toggle 22 to switch-in first motor 54A, and using trigger 28 to move wire element 42 distally until end-effector 44 is adjacent stone fragment 6; and/or using selection toggle 22 to switch-in second motor 54B, and using trigger 28 to rotate wire element 42 until stone fragment 6 is captured within end-effector 44. Each of these exemplary methods may be modified to account for variations of scope device 1 and peripheral device 40, and/or for use with peripheral device 140.

According to this disclosure, scope device 1 may be serve as a universal controller that is operable to control a plurality of devices, including delivery devices, display devices, visualization devices, and the like. The described aspects of scope device 1 provide the user with full control of each device, and the ability to adjust settings of the device, all without having to communicate with external operators and/or manipulate the specific controls of each device.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A scope device comprising:
a handle body extending along an axis between first end and a second end;
an actuator at the first end of the handle body;
a catheter at the second end of the handle body; and
a processor communicable with a plurality of devices to:
switch-in the actuator for control of one device of the plurality of devices;
configure, with the actuator, a setting of the one device,
control, with the actuator, the one device based on the setting, and
switch-in the actuator for control of another one of the plurality of devices,
wherein the processor is configured to receive a control mapping for each of the plurality of devices, and to apply the control mapping to the actuator to switch-in one or more of the devices, and
the actuator comprises a selection toggle operable with the processor to switch between the devices by switching between their respective control mappings.

2. The device of claim 1, further comprising:
a port on the second of the handle body; and
a lumen extending from the port, through the second end of the handle body, and through the catheter.

3. The device of claim 2, wherein the catheter includes a steerable portion, and the scope device further comprises a steering actuator operable to control the steerable portion of the catheter.

4. The device of claim 1, wherein the selection toggle includes one of a button, a joystick, a switch, and a trigger.

5. The device of claim 1, wherein the actuator comprises a program toggle operable with the processor to execute a control program for the one device.

6. The device of claim 1, wherein the processor communicable with the plurality of devices to switch-in the actuator for control of the one device together with at least one other device of the plurality devices.

7. The device of claim 1, wherein:
the one device includes a fluid source configured to deliver a fluid flow through the catheter; and
the processor is communicable with the fluid source to control, with the actuator, at least one property of the fluid flow.

8. The device of claim 7, wherein the at least one property of the fluid flow includes a flow rate or a pressure of the fluid flow.

9. The device of claim 1, wherein:
the one device includes a laser source configured to deliver laser energy through the catheter; and
the processor is communicable with the laser source to control, with the actuator, at least one property of the laser energy.

10. The device of claim 1, wherein:
the one device includes a peripheral device; and
the processor is communicable with the peripheral device to control, with the actuator, an electrical or mechanical component of the peripheral device.

11. The device of claim 1, wherein the actuator further comprises a plurality of controls, and wherein the processor is configured to use the control mappings to associate each of the plurality of controls with a particular function of the respective switched-in device.

12. A scope device comprising:
a handle body extending along an axis between first end and a second end;
a control actuator and a steering actuator at the first end of the handle body;
a catheter at the second end of the handle body, the catheter including a steerable portion operable with the steering actuator;
a port at the second end of the handle body;
a lumen extending from the port, through the second end of the handle body, and through the catheter; and
a processor communicable with a plurality of devices to:
switch-in the control actuator for control of one device of the plurality of devices;
configure, with the control actuator, a setting of the one device,
control, with the control actuator, the one device based on the setting, and
switch-in the control actuator for control of another one of the plurality of devices,
wherein the processor is configured to receive a control mapping for each of the plurality of devices, and apply the control mapping to the control actuator to switch-in one or more of the devices, and the control actuator comprises a selection toggle operable with the processor to switch between the control mappings of each of the plurality of devices.

13. The device of claim 12, wherein the control actuator further comprises a trigger that is pivotally mounted to the handle body, and operable to control the one device based on a rotational position of the trigger relative to the handle body.

14. The device of claim 13, wherein the control actuator further comprises a program toggle operable with the processor to execute a control program for the one device.

15. The device of claim 12, wherein:
the one device includes an imaging device; and
the processor is communicable with the imaging device to control, with the control actuator, activation of the imaging device.

16. The device of claim 12, wherein the processor remains in communication with at least one other device of the plurality of devices when the control actuator is switched-in for control of the one device.

17. The device of claim 12, wherein:
the one device includes (i) a fluid source configured to deliver a fluid flow through the lumen, and (ii) a laser source configured to deliver laser energy through the lumen; and
the processor is communicable with the fluid source and the laser source to control, with the control actuator, the fluid flow and the laser energy.

18. The device of claim 17, wherein the control actuator further comprises a program toggle operable with the processor to execute a control program for controlling the fluid source together with the laser source.

19. A scope device comprising:
a handle body extending along an axis between first end and a second end;
an actuator at the first end of the handle body;
a catheter at the second end of the handle body;
a peripheral device at the second end of the handle body, the peripheral device including a wire and a motor configured to move the wire relative to the catheter; and
a processor communicable with a plurality of devices to:
switch-in the actuator for control of one device of the plurality of devices;
configure, with the actuator, a setting of the one device,
control, with the actuator, the one device based on the setting, and
switch-in the actuator for control of another one of the plurality of devices,
wherein the one device includes the motor of the peripheral device, and
wherein the processor is configured to receive a control mapping for each of the plurality of devices, and to apply the control mapping to the actuator to switch-in one or more of the devices, and the actuator comprises a toggle operable with the processor to select the devices by selecting their respective control mappings.

20. The device of claim 19, wherein a distal end of the wire includes a basket, and the motor is configured to move the basket relative to the catheter.

* * * * *